United States Patent [19]

Yedid et al.

[11] Patent Number: 4,613,983
[45] Date of Patent: Sep. 23, 1986

[54] METHOD FOR PROCESSING X-RAY IMAGES
[75] Inventors: Henri Yedid, Issy les Moulineaux; Maurice Audoin, Bretigny sur Orge, both of France
[73] Assignee: Thomson CSF, Paris, France
[21] Appl. No.: 725,352
[22] Filed: Apr. 19, 1985
[30] Foreign Application Priority Data
May 25, 1984 [FR] France .................... 84 08253
[51] Int. Cl.$^4$ ............................................ H05G 1/64
[52] U.S. Cl. ....................................... 378/99; 358/111
[58] Field of Search ................. 378/99; 358/111, 181, 358/183

Primary Examiner—Craig E. Church
Assistant Examiner—John C. Freeman
Attorney, Agent, or Firm—Cushman, Darby & Cushman

[57] ABSTRACT

In order to reconstruct a composite X-ray image of larger size than the basic images obtained by radiography of the blood circulation system, the invention comprises the steps of picking-up and digitizing a predetermined number of basic images in respect of a number of relative positions between the patient-supporting table and an X-ray unit, in storing these images in a memory and in reconstructing a composite image, for example by transferring selected portions of the basic images into a collecting memory.

5 Claims, 3 Drawing Figures

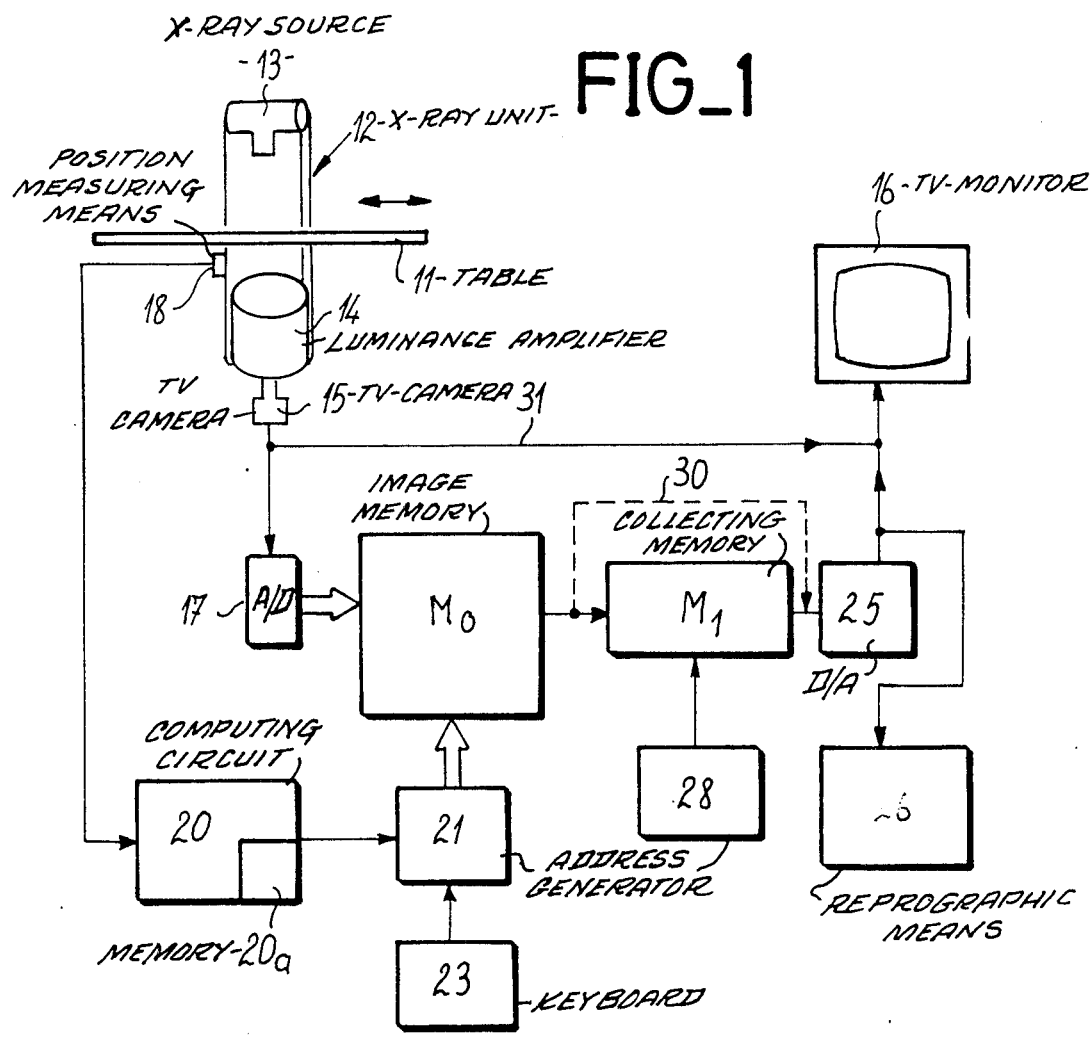
FIG_1
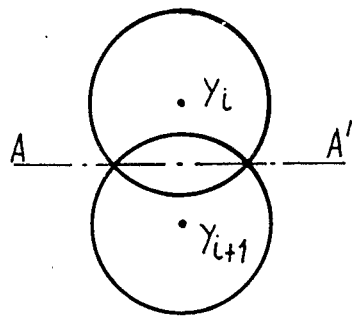
FIG_2

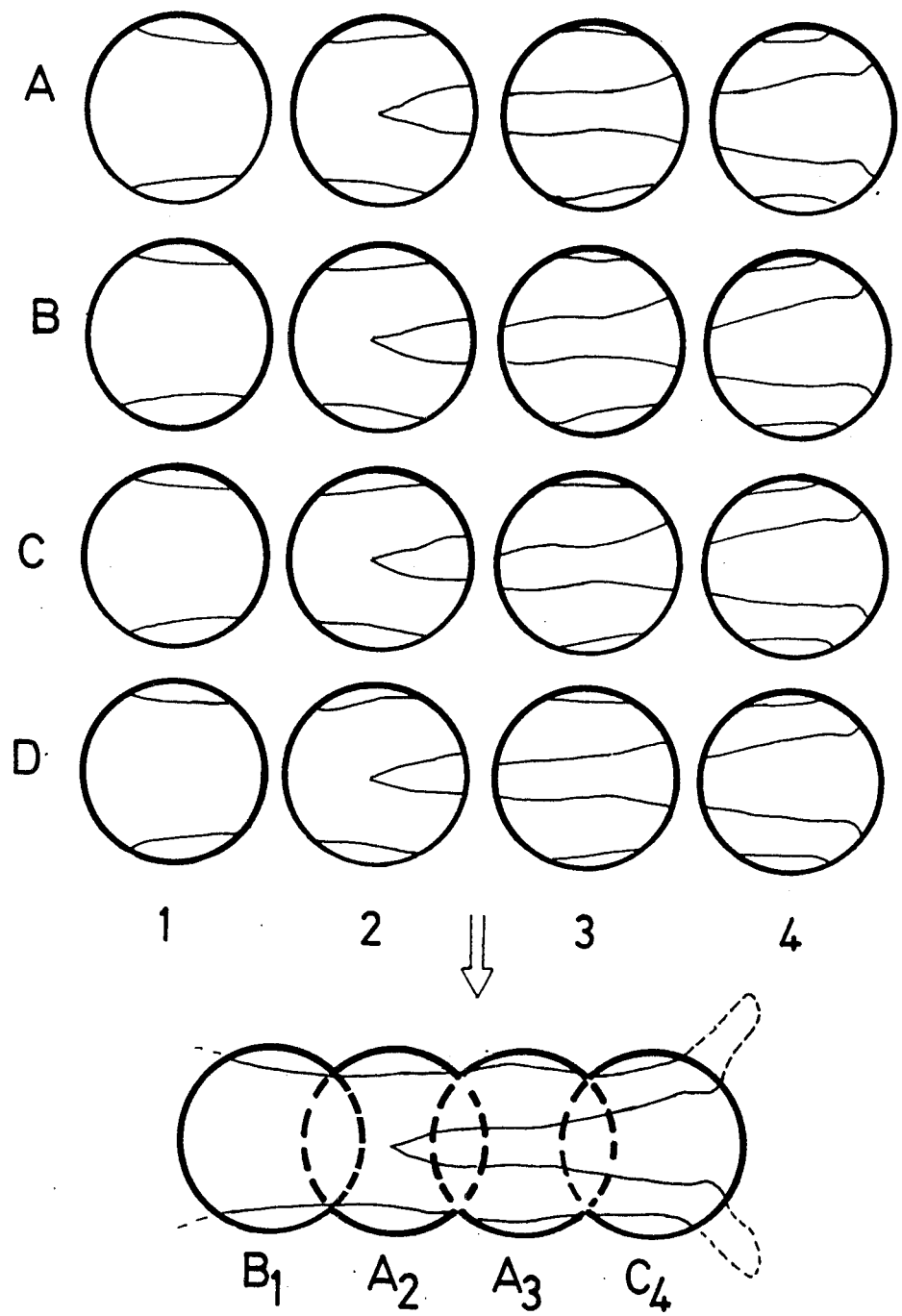

METHOD FOR PROCESSING X-RAY IMAGES

BACKGROUND OF THE INVENTION

1. Field of the Invention

This invention relates to a method for processing X-ray images with the main object of reconstructing a composite image, at least one dimension of which is appreciably larger than the visualization field of the receiver. By way of example, the receiver employed in this instance can be a luminance amplifier of a type known per se. The invention finds a preferred field of application in angiography, in particular for visualizing at least a large proportion of a patient's blood vessels and circulatory system.

2. Description of the Prior Art

In angiography, it is extremely useful to be able to display on a single document a large part of the arterial and/or venous system such as, in particular, the entire lower arterial and venous system. In the past, examinations of this type have been performed by means of an installation comprising an X-ray source placed at a considerable height above the patient in order to irradiate the entire region to be visualized as well as a film transfer mechanism for taking a series of adjacent photographs corresponding to different portions of this region. This system suffers from the double disadvantage of high operating costs arising from the considerable lengths of photographic film used and also arising from extensive irradiation of the patient. Furthermore, it is not always easy to read the document by reason of the variations in quality of the successive images. More recently, with the appearance of luminance amplifiers which tend to replace films, it has been proposed to take a number of photographs in respect of different relative positions between the source-receiver assembly and the patient-supporting table and to reproduce these photographs in adjacent relation on a single photographic document of distinctly smaller size than the series of photographs described above for an equivalent resolution of the image. Furthermore, the X-radiation dose applied to the patient is reduced to an appreciable extent. However, this type of presentation calls for an effort of mental reconstruction of the image on the part of the physician, which is considered as a restrictive condition.

SUMMARY OF THE INVENTION

The invention relates to an improvexent in the second type of method for preparation of the X-ray document described in the foregoing.

More specifically, the invention therefore relates to a method for processing X-ray images obtained in respect of different relative positions between a source-receiver assembly and a support for a body to be radiographed along a predetermined path, of the type which comprises storing each image in memory in the form of digital data which are representative of pixels of said images. The method essentially comprises the steps of obtaining overlapping images, in locating and storing said corresponding relative positions, in reading parts of the digital data of certain images, if necessary after processing, said parts being a function of said relative positions, and in converting the digital data of said parts to video signals for displaying a composite image formed by the joining-together of at least certain predetermined X-ray images aforesaid.

For the visual display of the reconstructed composite image by means of the television monitor, it is only necessary to displace this composite image over the television screen at low speed.

The basic elements of the invention as defined in the foregoing also permit the application of a novel method of formation of composite images involving the use of conventional techniques of logarithmic subtraction of images in which "masks" and images to be processed are produced in alternate sequence as the contrast product progresses within the patient's body.

In more precise terms, the invention is therefore concerned in addition with a method for processing images of a body within which a contrast product flows approximately in a direction parallel to the path aforesaid. The distinctive feature of the method in accordance with the foregoing definition lies in the fact that it comprises performing a single scan between said source-receiver assembly and the support for said body along said predetermined path, in picking-up two images and storing them in memory in respect of each relative position aforesaid, one image being produced in the absence of contrast product within the field of said image and the other image being produced in the presence of contrast product in part of said field, in carrying out in a manner known per se the subtraction of the two images picked-up at each relative position and in reading the aforementioned parts of the digital data of the images resulting from said subtractions.

It will be readily apparent that many alternative procedures are open to choice for carrying out the method in accordance with the invention. It is possible in particular to begin by reconstructing the two composite images in which the "masks" or images picked-up without any contrast product are grouped together in one composite image whilst the images picked-up with a contrast product are grouped together in the other composite image before performing the subtraction of the two composite images and displaying the result.

BRIEF DESCRIPTION OF THE DRAWINGS

Other features of the invention will be more apparent upon consideration of the following description and accompanying drawings, wherein:

FIG. 1 is a general block diagram of an X-ray installation for the practical application of the method in accordance with the invention;

FIG. 2 illustrates the processing operation carried out between two adjacent X-ray images;

FIG. 3 illustrates a complete image processing sequence in accordance with the invention.

DETAILED DESCRIPTION OF THE INVENTION

The installation of FIG. 1 comprises a patient-supporting table 11 and an X-ray unit 12 comprising an X-ray source 13 placed opposite to a luminance amplifier 14 which constitutes the X-ray image receiver mentioned earlier. The X-ray unit 12 and/or the table 11 are displaceable in translational motion along a predetermined rectilinear path in a direction parallel to the table. The luminance amplifier 14 is read by a television camera 15, the video output of which is connected to a television monitor 16 (direct connection 31) and to an analog-to-digital converter 17, the digital output of which is coupled with an image memory $M_O$. Measuring means 18 for measuring the relative displacement between the table 11 and the X-ray unit 12 are connected to a computing unit 20 for controlling an address generator 21 which initiates reading of selected portions of the memory $M_O$. The address generator 21 is also coupled with a selecting keyboard 23 used by the operator for selecting a predetermined number of images prerecorded in the memory $M_O$ and for reading said images line by line and pixel by pixel, in a predetermined order. The memory $M_O$ is coupled with a collecting memory $M_1$ in which certain images or parts of images may be transferred under the control of the address generator 21 and of the keyboard 23. The output of the memory $M_1$ is connected to a digital-to-analog converter 25, the output of which controls the monitor 16 and a reprographic means 26 which preferably consists in this case of a device of a type known per se for reproduction of video images by laser printing. By way of example, a device which is well suited for this application is proposed by the Soro Company.

All the means which have just been described are individually known except for the computing unit 20 which will hereinafter be described in greater detail. This unit receives via the measuring means 18 data representing the relative positioning between the table 11 and the unit 12 at the moments of picking-up of images. These data can be stored in a memory storage unit $20_a$ and the computing unit 20 is arranged and programmed for controlling the address generator 21 in such a manner as to carry out selective readout of the memory $M_O$ and thus to read only the data which are representative of the pixels located in specific regions of the different images as a function of the data stored in the memory $20_a$.

FIG. 2 illustrates this selective readout. In accordance with conventional practice, the luminance amplifier delivers a circular image which is characterized by the position of its center $Y_i$ and by its constant diameter. In the case of all images read and stored, the positions of these centers $Y_i$ with respect to a common origin are stored in memory (memory $20_a$). Since the diameter of each image is known and preprogrammed, the overlap values between adjacent images can readily be determined by means of these data alone in order to decide on which pixels are to be read from each portion of the memory $M_O$ in which the data relating to a given image are written with a view to transmitting them to the memory $M_1$. For example, if the images are read line by line (which corresponds to the conventional mode of display produced by scanning of the television monitor 16) and if the lines of two adjacent images which pass through the centers of these images correspond respectively to the positions $Y_i$ and $Y_i+1$ along the path mentioned earlier, the line A-A' which joins the two points of intersection of the limits of the images along the same path will correspond to the position $(Y_i+Y_i+1)/2$ and will be the boundary line to be adopted between the two images. It will therefore only be necessary to collect the digital data from the lines of the video image located on one side of said line A-A' in an image (FIG. 2) and to collect the digital data from the lines located on the other side of the saxe line A-A' in the other adjacent image and to transfer these selected data into the memory $M_1$ in order to reconstruct the desired composite image from a plurality of adjacent elementary images.

It follows from the foregoing that the design concept of the computing circuit 20 is within the capacity of any one versed in the art since it is limited to the use of simple computing means for receiving the stored values in the memory $20_a$ and means for controlling the address generator 21. From a structural standpoint, the memory $20_a$ can form part of the memory $M_O$ whilst the computing circuit 20 can be wired or formed by a subprogram. The memory $M_1$ is read cyclically while being controlled by an address generator 28 (refreshable memory) for permitting continuous display on the television monitor 16 after conversion of the digital data (digital-to-analog converter 25) to a video signal. Since the capacity of the memory $M_1$ is that of a number of images of the same size as the television monitor, the address generator 28 is programmed so as to produce a relative displacement of one or a number of lines at each read operation, thereby ensuring that the entire composite image passes slowly across the screen of the television monitor 16. The memory $M_1$ can also be dispensed with if the address generator 21 is programmed so that the useful portions of the image displayed at each instant may be read successively and directly from the memory $M_O$. It is also wholly possible without thereby departing from the scope of the invention to choose different geometrical limits between the overlapping images. For example, it is possible to record all the pixels of the first image and then the pixels of the second image which are located outside the perimeter of the first image, and so forth. The computing circuit is then modified so as to determine and convert to digital data the equation of the circular arc which marks the boundary between the two images and so as to select the pixels by means of a classification of the addresses of these latter with respect to said boundary curve. As will be readily apparent, the method can readily be transposed for the reconstruction of composite images from square or rectangular images.

FIG. 3 illustrates an advantageous application of the method in accordance with the invention for the use of a number of sequences of image pickup and storage corresponding to successive scans between the table 11 and the X-ray unit 12. It is assumed for example that there have thus been formed four groups A, B, C, D each comprising four overlapping images. Thus each group reconstructs the entire lower portion of a patient's body for a complete examination of the circulatory system. These different images are picked-up approximately in the same positions (these positions being four in number in the example illustrated) along the path of displacement and are stored in the memory $M_O$.

The operator then has the possibility of displaying said images one by one by means of a direct connection 30 which is switchable between the output of the memory $M_O$ and the digital-to-analog converter 25. Thus the operator can select from each group those images which can most readily be utilized and can transfer the corresponding information into the memory $M_1$ while at the same time forming the "cutouts" which result from the method defined in the foregoing. Thus in the example shown in the drawings, the operator has successively selected the images $B_1$, $A_2$, $A_3$ and $C_4$. It will of course be understood that, if provision is not made for a memory $M_1$, the selected digital data can be read cyclically and directly from the memory $M_O$ as mentioned earlier. Independently of the visual display of the composite image which is contained in the memory $M_O$ and which passes slowly across the screen of the television monitor 16, the reprographic means 26 can be utilized at any moment for instantaneously delivering a printout of the same image.

The invention also covers an additional application which makes use of well-known techniques for processing X-ray images by subtraction of two images, one of the images or "mask" being picked-up without any contrast product (that is to say prior to arrival of said contrast product in the field of the receiver 14) and the other image being picked-up after arrival of the contrast product in said field. The means for processing by subtraction can be integrated with the installation of FIG. 1 without any difficulty. The initial step consists in injecting a dose of contrast product into the patient. A single scan is then performed between the X-ray unit 12 and the table 11 while picking-up two images for each position chosen. Prior to recording of any image, the field of view corresponding to this image is continuously observed by radioscopy (direct connection 31 between the output of the camera 15 and the television monitor 16). After injection of the product, the first image is picked-up and stored in memory, preferably a short time before said contrast product penetrates into the field of the image under observation. A second image is then picked-up and stored in the same position when the contrast product has spread over a certain part of the field of the image. A subtraction of these two images picked-up in the same position makes it possible to improve the visual display of the circulatory system in the portion corresponding to the presence of the contrast product. This portion is stored in the memory $M_1$. A new relative position is then sought between the X-ray unit and the table with a view to ensuring that the image displayed in radioscopy is substantially free of contrast product. The same operations are then repeated for the purpose of transferring another portion of the composite image processed in the memory $M_1$, and so on in sequence. It will readily be apparent that certain operations may be reversed. For example, it is wholly feasible to reconstruct a complete composite "mask" image (from all the images picked-up without any contrast product and stored in memory throughout the sequence) and a complete composite image with contrast product before subtracting one composite image from the other.

What is claimed is:

1. A method for processing X-ray images obtained in respect of different relative positions between a source-receiver assembly and a support for a body to be radiographed along a predetermined path, of the type which comprises storing each image in memory in the form of digital data which are representative of pixels of said images, wherein said method comprises the steps of obtaining overlapping images, in locating and storing said corresponding relative positions, in reading parts of the digital data of certain images, said parts being a function of said relative positions, and in converting the digital data of said parts to video signals for displaying a composite image formed by the joining-together of at least certain predetermined X-ray images aforesaid.

2. A method for processing X-ray images according to claim 1, wherein said method comprises performing a plurality of scans between said source-receiver assembly and a body support along said predetermined path, in picking-up and storing series of respective images during successive scans and in selecting a sequence of overlapping images from said series of images before reading the aforesaid parts of the digital data of each image of said sequence.

3. A method for processing images according to claim 1, wherein said method comprises applying the video signals of said composite image to reprographic means.

4. A method according to claim 1 for processing X-ray images of a body within which a contrast product flows approximately in the direction of said path, wherein said method comprises performing a single scan between said source-receiver assembly and said body support along said path, in picking-up and storing two images in respect of each relative position aforesaid, one image being produced in the absence of contrast product within the field of said image and the other image being produced in the presence of contrast product in at least part of said field, in carrying out the subtraction of the two images picked-up at each relative position and in reading the aforementioned parts of the digital data of the images resulting from said subtractions.

5. A method according to claim 1 for processing X-ray images of a body within which a contrast product flows approximately in the direction of said path, wherein said method comprises performing a single scan between said source-receiver assembly and said body support along said path, in picking-up and storing two images in respect of each relative position aforesaid, one image being produced in the absence of contrast product within the field of said image and the other image being produced in the presence of contrast product in at least part of said field, in reading the aforementioned parts of the digital data which are representative of these two types of images respectively for the purpose of reconstructing two composite images aforesaid and subtracting one composite image from the other.

* * * * *